US010719308B1

(12) United States Patent
Putre et al.

(10) Patent No.: US 10,719,308 B1
(45) Date of Patent: Jul. 21, 2020

(54) SYSTEM AND METHOD FOR DYNAMICALLY MONITORING A CONFIGURATION OF A SERVER COMPUTING DEVICE

(71) Applicant: Allscripts Software, LLC, Raleigh, NC (US)

(72) Inventors: Peter C. Putre, Shelburne, VT (US); Heidi Birchard Turner, Hinesburg, VT (US); Christopher P. Trapeni, Shelburne, VT (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 204 days.

(21) Appl. No.: 15/804,163

(22) Filed: Nov. 6, 2017

(51) Int. Cl.
*G06F 8/65* (2018.01)
*G06F 8/71* (2018.01)
*G16H 10/60* (2018.01)
*G16H 40/63* (2018.01)

(52) U.S. Cl.
CPC ............... *G06F 8/65* (2013.01); *G06F 8/71* (2013.01); *G16H 10/60* (2018.01); *G16H 40/63* (2018.01)

(58) Field of Classification Search
CPC .. G06F 8/65; G06F 8/71; G16H 10/60; G16H 40/63
USPC ........................................................ 717/171
See application file for complete search history.

(56) References Cited

U.S. PATENT DOCUMENTS

| 6,560,699 | B1 * | 5/2003 | Konkle | G06F 9/44505 |
| | | | | 713/1 |
| 7,181,505 | B2 * | 2/2007 | Haller | A61B 5/0031 |
| | | | | 709/219 |
| 7,523,118 | B2 | 4/2009 | Friedlander et al. | |
| 9,152,534 | B2 | 10/2015 | Balla et al. | |

(Continued)

FOREIGN PATENT DOCUMENTS

| CA | 2366300 A1 * | 9/2000 | ......... G06F 19/3418 |
| CN | 1255743 C * | 5/2006 | ............. G16H 40/63 |

OTHER PUBLICATIONS

Marsolo et al., "Clinical genomics in the world of the electronic health record", Oct. 2013, Genetics in Medicine, vol. 15, No. 10 (Year: 2013).*

(Continued)

*Primary Examiner* — Wei Y Zhen
*Assistant Examiner* — Junchun Wu
(74) *Attorney, Agent, or Firm* — Medley, Behrens & Lewis, LLC (57) ABSTRACT

Described herein are features pertaining to generating and presenting a log entry based upon configuration data received from a monitoring service of an electronic health record application (EHR) executing at a server computing device. A monitoring application can receive configuration data from the server computing device that hosts a feature of an EHR that is implemented in a healthcare enterprise, wherein the configuration data comprises an indication of a modification to the server computing device, and further wherein the monitoring application is configured to facilitate presenting the modification to an EHR support engineer. Exemplary modifications to the server computing device can be: a hardware change to the server computing device (e.g., replacement of a processor, addition of RAM, etc.), an (Continued)

upgrade to a feature hosted by the EHR on the server computing device, etc.

17 Claims, 5 Drawing Sheets

(56) References Cited

U.S. PATENT DOCUMENTS

| | | | |
|---|---|---|---|
| 10,242,755 B2* | 3/2019 | Lloyd | G06F 16/258 |
| 2006/0010015 A1* | 1/2006 | Thomas | G06Q 10/10 |
| | | | 705/3 |
| 2006/0184714 A1* | 8/2006 | Dang | G06F 8/65 |
| | | | 711/100 |
| 2008/0148231 A1* | 6/2008 | Weber | G06F 11/324 |
| | | | 717/120 |
| 2011/0060607 A1* | 3/2011 | Kesselman | G06Q 10/10 |
| | | | 705/3 |
| 2011/0246224 A1 | 10/2011 | Green, III et al. | |
| 2012/0059668 A1* | 3/2012 | Baldock | G06Q 50/24 |
| | | | 705/3 |
| 2012/0059911 A1* | 3/2012 | Randhawa | G16H 30/20 |
| | | | 709/219 |
| 2012/0185925 A1 | 7/2012 | Barkie et al. | |
| 2012/0215857 A1* | 8/2012 | Bohner | G16H 40/20 |
| | | | 709/206 |
| 2013/0173300 A1* | 7/2013 | Hyde | G16H 10/60 |
| | | | 705/3 |
| 2015/0213195 A1* | 7/2015 | Blechman | G16H 10/60 |
| | | | 705/51 |
| 2015/0370968 A1* | 12/2015 | Addis | G16H 10/60 |
| | | | 705/3 |
| 2016/0042124 A1 | 2/2016 | Douglass et al. | |
| 2016/0378462 A1* | 12/2016 | Hu | H04L 67/34 |
| | | | 717/173 |
| 2017/0048323 A1* | 2/2017 | Schlapfer | H04L 67/02 |
| 2018/0184905 A1* | 7/2018 | Riebel | G16H 10/60 |

OTHER PUBLICATIONS

Fabian et al., "Collaborative and secure sharing of healthcare data in multi-clouds", 2014, Elsevier Ltd. (Year: 2014).*

Liu et al., "e-Healthcare Security Solution Framework", 2012, IEEE (Year: 2012).*

Sittig et al., "Improving the safety of health information technology requires shared responsibility: It is time we all step up", Jun. 2017, Elsevier Inc. (Year: 2017).*

* cited by examiner

SYSTEM AND METHOD FOR DYNAMICALLY MONITORING A CONFIGURATION OF A SERVER COMPUTING DEVICE

BACKGROUND

Electronic health record applications (EHRs) are robust applications that are utilized in medical facilities across a variety of aspects of a medical practice. For example, and not by way of limitation, an EHR can include features related to managing patient data, supplementing patient care, referring patients, etc. Generally, when an EHR provider initially implements an EHR in a healthcare enterprise (e.g., hospital environment, physician's office, etc.), components that host features of the EHR are installed and executed among a plurality of networked computing devices, thereby allowing end users at client computing devices of the healthcare enterprise to access the features of the EHR. At the initial implementation of the EHR within the healthcare enterprise, the EHR provider can manually document configuration settings of the networked computing devices (e.g., hardware specifications, software specifications, network addresses, etc.) in a configurations file. Based upon the configurations file, the EHR provider can provide troubleshooting, hardware upgrades to a networked computing device, software updates to the EHR, etc., to the healthcare enterprise.

Oftentimes, the aforementioned configurations file becomes inaccurate as modifications to computing devices (in the plurality of networked computing devices) of the healthcare enterprise occur, wherein the computing devices host features of the EHR. Exemplary modifications to the computing device include: a hardware change to the computing device (e.g., replacement of a processor, addition of RAM, etc.), an upgrade to the feature hosted by the EHR, etc. Further, networked computing devices can be added or removed over time, may be upgraded to different software versions, and so forth. The approach of manually documenting configuration settings is associated with numerous problems, including but not limited to individuals improperly documenting configurations, the lack of guarantee that manually documented information is correct, etc., which negatively impacts support and upgrade teams for the EHR.

SUMMARY

The following is a brief summary of subject matter that is described in greater detail herein. This summary is not intended to be limiting as to the scope of the claims.

Described herein are various technologies pertaining to computer executable applications that are well-suited for use in a healthcare environment. More specifically, described herein are various technologies pertaining to a computer system, wherein a computer-executable monitoring application can receive configuration data from a server computing device that hosts a feature of an EHR that is implemented in a healthcare enterprise, wherein the configuration data comprises an indication of a modification to the server computing device, and further wherein the monitoring application is configured to present the modification to an EHR provider. More particularly, the monitoring application is configured to receive configuration data from a monitoring service of the EHR that is executing on the server computing device, where the monitoring service generates the configuration data responsive to the modification to the server computing device occurring. Exemplary modifications to the server computing device can be: a hardware change to the server computing device (e.g., replacement of a processor, addition of RAM, etc.), an upgrade to a feature hosted by the EHR on the server computing device, etc. The configuration data additionally includes an identifier of a healthcare enterprise where the EHR is installed and implemented. The monitoring service is configured to transmit the configuration data to the monitoring application by way of, e.g., a network connection.

Responsive to receiving the configuration data, the monitoring application is configured to generate a log entry, wherein the log entry includes an indication of the modification to the server computing device. The log entry can additionally include an indicator of the healthcare enterprise that uses the server computing device as well as temporal information that indicates when the modification occurred. Further, the monitoring application is configured to store the log entry in a log store based upon the identifier of the healthcare enterprise, wherein the log store includes a plurality of log entries that include the identifier of the healthcare enterprise. The monitoring application can generate and store additional log entries from additional monitoring services that are executing on additional server computing devices that hosts features of the EHR for the healthcare enterprise, wherein the log entries include indications of modifications to the server computing devices of the healthcare enterprise (that are executing the EHR).

The monitoring application can be configured to cause a graphical user interface (GUI) to be displayed on a display, wherein the GUI includes visual representations of the log entries of the log store. Additionally, the monitoring application can be configured to generate and transmit notifications (e.g., email alerts, SMS text messages, etc.) to computing devices that indicate that a modification has occurred, wherein the modification falls within a user-selected category of modifications.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to a monitoring application that is in network communication with a monitoring service of an electronic health record application (EHR) are described herein, wherein the monitoring application receives configuration data from the monitoring service, and further wherein the configuration data includes an indication that a modification to a server computing device that executes the EHR has occurred. The technologies are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Further, as used herein, the term "exemplary" is intended to mean serving as an illustration or example of something, and is not intended to indicate a preference.

Further, as used herein, the terms "component", "system", "feature", and "service" are intended to encompass instructions stored in computer-readable data storage that are configured to cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Generally, the features described herein pertain to technologies for generating and presenting a log entry based upon configuration data received from a monitoring service of an EHR executing at a server computing device. More particularly, a monitoring application can receive configuration data from the server computing device that hosts a feature of an EHR that is implemented for a healthcare enterprise, wherein the configuration data comprises an indication of a modification to the server computing device, and further wherein the monitoring application is configured to cause the modification be presented in a graphical user interface (GUI) shown at a client computing device operated by a support staff person of the EHR provider. Exemplary modifications to the server computing device can be: a hardware change to the server computing device (e.g., replacement of a processor, addition of RAM, etc.), an upgrade to a feature hosted by the EHR on the server computing device, etc.

The monitoring application can be configured to generate a plurality of log entries based upon configuration data that is received from a plurality of monitoring services, wherein the monitoring services are executed by a plurality of server computing devices that are executing various features of the EHR. Further, the monitoring application can store the plurality of log entries in a log store based upon a common identifier (e.g., which identifies the healthcare enterprise) in the log entry. The monitoring service can present the plurality of log entries (in the log store) that accurately reflect an up-to-date state of the EHR of the healthcare enterprise. Based upon the presentation of the log entries, the EHR provider can provide troubleshooting, hardware upgrades to a networked computing device, software updates to the EHR, etc., to the healthcare enterprise. Additionally, the monitoring application can be configured to generate and transmit notifications (e.g., email alerts, SMS text messages, etc.) to computing devices that indicate that a modification has occurred, wherein the modification falls within a user-selected category of modifications.

Figure 1:
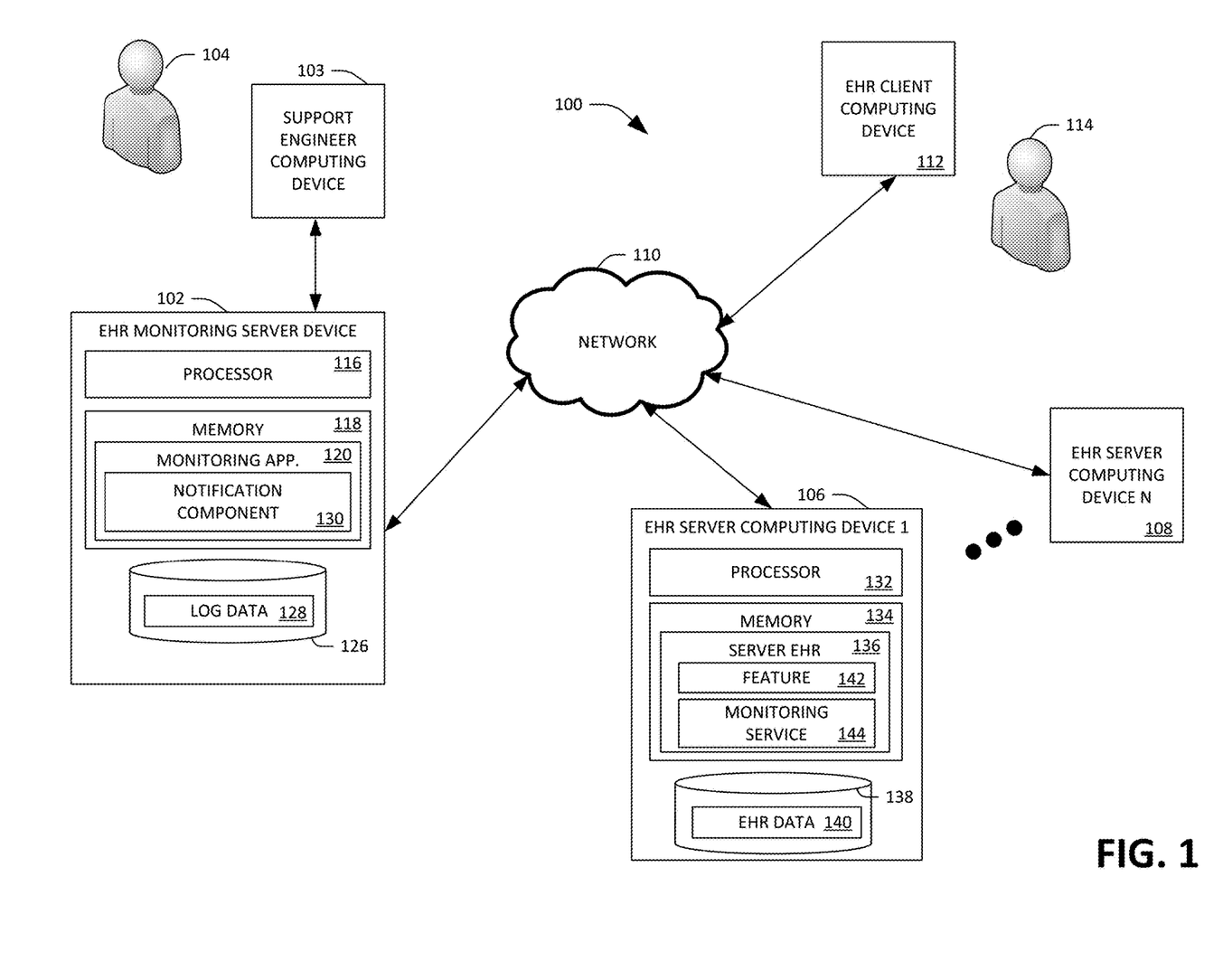
FIG. 1 is a functional block diagram of an exemplary system that that facilitates generating and presenting a log entry based upon configuration data received from a monitoring service of an electronic health record application (EHR) executing at a server computing device, wherein the configuration data includes an indication of a modification to the server computing device.

With reference now to FIG. 1, an exemplary system 100 that facilitates generating and presenting a log entry based upon configuration data received from a monitoring service of an EHR executing at a server computing device is illustrated, wherein the configuration data includes an indication of a modification to the server computing device. The system 100 includes an EHR monitoring server device 102 and a support engineer computing device 103 that is in communication with the EHR monitoring server device 102. The support engineer computing device 103 is operated by an EHR support engineer 104. The EHR support engineer 104 may be tasked with providing support or upgrading a feature of one or more EHRs that are implemented at one or more healthcare enterprises. The support engineer computing device 103 may be any suitable type of client computing device, including a desktop computing device, a laptop computing device, a mobile telephone, a tablet computing device, a wearable computing device, or the like.

The system 100 further includes a plurality of EHR server computing devices 106-108 that are in communication with the EHR monitoring server device 102 by way of a suitable network 110, such as the Internet, an intranet, or the like. An EHR server computing device 106 (in the plurality of EHR server computing devices 106-108) is generally configured to host a feature of an EHR that is implemented at a healthcare enterprise. While the server computing devices 106-108 are described herein as hosting EHR features for one healthcare enterprise, it is to be understood that the EHR monitoring server device 102 can be in network communication with server computing devices that host EHR features for EHRs implemented at many different healthcare enterprises. Hence, the support engineer 104 may be employed by a provider of the EHR, wherein the EHR (e.g., different versions of the EHR) are implemented at different facilities. Features of the EHR hosted at the server computing devices 106-108 can include, but are not limited to, a web service feature (e.g., managing patient data, supplementing patient care, referring patients), a database (e.g., SQL), a messaging application, etc. As will be described in greater detail herein, the EHR server computing devices 106-108 are additionally configured to transmit configuration data to the EHR monitoring server device 102.

The system 100 additionally includes an EHR client computing device 112 that is operated by a healthcare worker 114 (e.g., a clinician, a billing specialist, etc.). The healthcare worker 114 may be utilizing the EHR client computing device 112 in connection with providing care to a patient. The EHR client computing device 112 is in communication with the plurality of EHR server computing devices 106-108 (by way of, e.g., the network 110 or other suitable network) and is configured to allow the healthcare worker 114 to access features hosted on the EHR server computing devices 106-108. The EHR client computing device 112 operated by the healthcare worker 114 may be any suitable type of client computing device, including a desktop computing device, a laptop computing device, a mobile telephone, a tablet computing device, a wearable computing device, or the like. Further, while the EHR monitoring computing server 102 and the EHR client computing device 112 are depicted as being in communication with the server computing devices 106-108 by way of the network 110, it is to be understood that the EHR monitoring server device 102 and the EHR client computing device 112 may be in communication with the server computing devices 108-110 over different networks.

The EHR monitoring server device 102 includes a processor 116 and memory 118. The memory 118 stores instructions that are executed by the processor 116. More specifically, the memory 118 includes a monitoring application 120. The EHR monitoring server device 102 additionally includes a data store 126 that can store log data 128 (e.g., a plurality of log stores), wherein a log store in the log stores is a repository for log entries that are based upon configuration updates received from the EHR server computing devices 106-108 of the healthcare enterprise. A log entry includes data that is indicative of a modification to an EHR server computing device that generated a configuration update. As will be described in greater detail herein, the monitoring application 120 is generally configured to generate the log entry based upon configuration data that is received from an EHR server computing device in the plurality of EHR server computing devices 106-108. Additionally, the monitoring application 120 can be configured to cause the log entry to be presented in a graphical user interface (GUI) at the support engineer computing device 103. Further, a notification component 130 of the monitoring application 120 can be configured to generate and transmit a notification of the log entry to the support engineer computing device 103.

The EHR server computing device 106 comprises a processor 132 and memory 134 that stores instructions that are executed by the processor 132. As shown in FIG. 1, the memory 134 includes at least a portion of a server EHR 136. The EHR server computing device 106 further comprises a data store 138 that comprises EHR data 140. The server EHR 136 includes a feature 142 and a monitoring service 144. The feature 142 can be any feature that is provided by EHRs to a healthcare enterprise. The feature 142 of the EHR can be, for example, a web service component (e.g., managing patient data, supplementing patient care, referring patients), a database component (e.g., SQL), a messaging application, etc.

In a more specific example where the feature 142 is hosting and managing patient data in the EHR data 140, the feature 142 causes the EHR server computing device 106 to host the patient data and provide appropriate patient data to a client EHR executing on the EHR client computing device 112 responsive to receipt of a request from the client EHR of the patient data. The client EHR is an application executing on the client computing device 112, which is employed to interface with the server EHR 136. Therefore, the client EHR can be a web application executing in a browser, a standalone application, etc. Generally, the healthcare worker 114 can interact with the client EHR executing on the EHR client computing device 112, which causes the client EHR to transmit data to the server EHR 136 executing on the EHR server computing device 106. Content of the data transmitted from the client EHR to the server EHR 136 can include, for instance, data that identifies the healthcare worker 114 and data that identifies a patient (to whom the healthcare worker 114 is providing), amongst other data. Responsive to receipt of such data, the server EHR 136, in accordance with the feature 142, can construct a query based upon the data and search over the EHR data 140 (e.g., in the date store 138) based upon the query, thereby obtaining search results. The EHR data 140 can include any suitable data that is used in connection with provision of care to the patient, including for a feature related to presenting an electronic patient record for the patient. The server EHR 136 can cause the EHR server computing device 106 to transmit the search results to the EHR client computing device 112, whereupon the search results are provided to the client EHR. The client EHR subsequently causes at least a portion of the search results (that comprise the electronic patient record) to be presented in graphical data of a display of the EHR client computing device 112.

The monitoring service 144 is configured to, responsive to detecting a modification to the EHR server computing device 106, generate configuration data that comprises an indication of the modification and transmit the configuration data to the EHR monitoring server device 102. Exemplary modifications to the EHR server computing device 106 can be: a hardware change to the server computing device (e.g., replacement of a processor, addition of RAM, etc.), an upgrade to a feature of the HER hosted at the server computing device, etc. The configuration data additionally includes an identifier of a healthcare enterprise where the EHR is installed and implemented. Additionally, the monitoring service 144 can include identification information of the EHR server computing device 106 in the configuration data, wherein such identification information allows the EHR support engineer 104 to ascertain information regarding the modification to the EHR server computing device 106 or monitor a state of the plurality EHR server computing devices 106-108 (e.g., determine whether an EHR server computing device is operating correctly). For example, the identification information can include: a name, a server type, a status, network information (e.g., IP address), hardware information (e.g., processor), and file system information of the EHR server computing device 106. While the monitoring service 144 is illustrated as being a part of the server EHR 136, it is to be understood that the monitoring service 144 may be built into an operating system of the EHR server computing device 106, may be a separate application from the server EHR 136, etc.

Operation of the monitoring application 120 and the monitoring service 144 is now described. Generally, the monitoring application 120 and the monitoring service 144, together, facilitate creation and management of a dynamic configurations file that represents an accurate, current state of an EHR of a healthcare enterprise. An EHR support engineer can provide troubleshooting, hardware upgrades to a networked computing device, software updates to the EHR, etc., to the healthcare enterprise based upon the dynamic configurations file.

The monitoring application 120 of the EHR monitoring server device 102 is configured to receive configuration data from monitoring services that are executing on the plurality of the EHR server computing devices 106-108. As described previously, the monitoring service 144 is configure to, responsive to detecting a modification to the EHR server computing device 106, generate configuration data that includes an indication of the modification that occurred as well as an identifier of the healthcare enterprise where the EHR server computing device 106 is implemented. With more particularity, the monitoring service 144 runs in the background on the server computing device 106, and gathers configuration data that is specific to the EHR server computing device 106 and its configuration. In a non-limiting example, EHR server computing device 106 can run the monitoring service 144 on an hourly basis, and the monitoring service 144 can gather data from the registry, configuration files, and dynamic-link libraries (dlls), and can further cause the EHR server computing device 106 to push this data (configuration data) to the monitoring application 120 executing on the EHR monitoring server computing device 102. The configuration data may include identification information, e.g., a name, a server, etc. or specification information (e.g., identification of hardware components, IP addresses, etc.) of the EHR server computing device 106.

Responsive to receiving the configuration data, the monitoring application 120 of the EHR monitoring computing device 102 is configured to generate a log entry when the received configuration data for the EHR server computing device 106 is different from configuration data most recently received from the monitoring service 144 executing on the EHR server computing device 106. For example, the monitoring application 120 receives the configuration data and generates a hash value for the configuration data; the monitoring application 120 accesses a database (e.g., a SQL database), and retrieves a most recent hash value for the EHR server computing device 106, if any. The database may also be referred to as a "log store." If there is no row in the database for the EHR server computing device 106, the monitoring application 120 adds a row into such database, where the row includes the hash value and all of the configuration data. When the database includes a row for the EHR server computing device 106, the monitoring application 120 compares the hash value that exists in the (most recently added) row of the database with the hash value generated based upon the configuration data just received from the EHR server computing device 106. When the hash values are the same, the monitoring application 120 takes no further action. When the hash values are different, however, the monitoring application 120 adds a new row to the database, where this new row includes the newly-generated hash value and the configuration data upon which this hash value is based. Accordingly, the new row can be referred to as a log entry that includes an indication of the modification to the EHR server computing device 106 and an indication of the healthcare enterprise that uses the server computing device (identified based upon the identifier).

The monitoring application 120 can also append, to the log entry, temporal information that indicates when the modification occurred or when the configuration data was received. Further, the monitoring application 120 is configured to store the log entry in a log store based upon the identifier of the healthcare enterprise (from which the EHR server computing device 106 is from), wherein the log store includes a plurality of log entries that include the indicator of the healthcare enterprise. The log store can be stored in, e.g., the log data 128 of the EHR monitoring computing device 102. As noted above, the log store can be a database that can be modified base on SQL commands. In operation, the log store comprises multiple log entries that are based upon configuration data generated by monitoring services of the plurality of EHR server computing devices 106-108, wherein the log entries each indicate a modification to an EHR server computing device. The log data 128 can also include log stores for other healthcare enterprises that utilize the EHR developed by the EHR provider.

Figure 2:
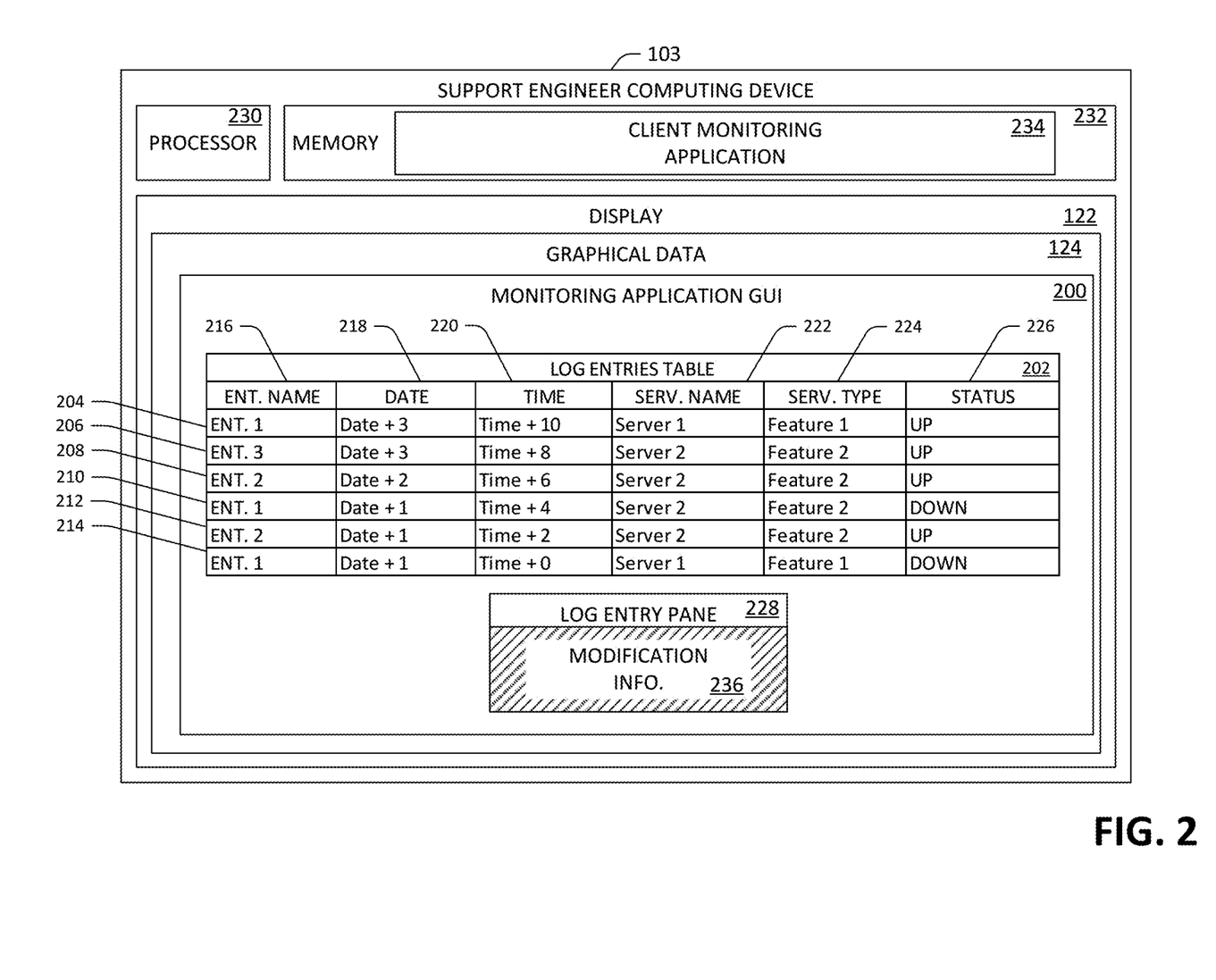
FIG. 2 depicts an exemplary EHR monitoring client computing device.

The log data 128 can also include a notification table, wherein the monitoring application 120 can update the notification table when a configuration change to one or more of the server computing devices 106-108 is detected. The monitoring application 120 can periodically analyze the notification table and transmit notifications to appropriate computing devices. For instance, the monitoring application 120 can be configured to present a graphical representation of the log stores in the log data 128 to the EHR support engineer 104 based upon alterations represented in the notification table. With reference now to FIG. 2, a functional block diagram of the support engineer computing device 103 is illustrated. The support engineer computing device 103 comprises a processor 230 and memory 232, wherein the memory 232 includes a client monitoring application 234 loaded therein. The client monitoring application 234, when executed by the processor 230, is configured to interface with the monitoring application 120 executing on the EHR monitoring server device 102. With more specificity, the processor 230, when executing the client monitoring application 234, causes a monitoring application GUI 200 to be included in graphical data 124 on a display 122 of the support engineer computing device 103. In this example, the monitoring application GUI 200 comprises a log entries table 202, wherein the log entries table 202 is a graphical representation of at least a portion of at least one log store that is generated based upon the log entries that are stored in the log data 128 of the EHR monitoring server device 102.

The log entries table 202 includes rows 204-214, wherein each row in the rows includes a log entry in the log stores. Additionally, values in the rows 204-214 can be represented in exemplary columns, where the columns include a column 216 for identifiers of healthcare enterprises, a column 218 for dates of log entries, a column 220 for columns of log entries, a column 222 for server names that generated configuration data from which the long entries were generated, a column 224 for identities of server type (e.g., feature) for log entries, and a column 226 that identifies status of a feature. A value in the column 216 are indicative of a healthcare enterprise (e.g., hospital environment, physician's office, etc.) where an EHR is installed, where the monitoring application 120 is configured to monitor the EHR. As shown in FIG. 2, the log entries table 202 can include log entries from a first healthcare enterprise, a second healthcare enterprise, and a third healthcare enterprise. A value in the column 218 column and a value in the column 220 can, respectively, be a date stamp and a timestamp for when the configuration data (from which a log entry is generated) is received. Alternatively, the date stamps and timestamps can be transmitted in the configuration data that indicate when a modification has occurred.

A value in the column 222 can include a name of an EHR server computing device that transmitted configuration data (from which a log entry is generated). Naming schemes can be specific to a healthcare enterprise. Alternatively, an EHR provider can configure the monitoring application 120 to implement a uniform naming mechanism for names of the EHR server computing devices. A values in the column 224 can identify a feature that an EHR server computing device hosts. A value in the column 226 can identify a status of an EHR server computing device, or a feature hosted by the EHR server computing device, that transmitted configuration data (from which a log entry is generated). As shown in FIG. 2, values of "UP" and "DOWN" indicate whether an EHR server computing device (or feature) is operational or non-operational. A value in the column 226 can additionally describe the modification to the EHR server computing device (e.g., descriptive text that describes the modification).

Additionally, the client monitoring application 234 can be configured to detect input (e.g., touch-input, a mouse click, etc.) of the EHR support engineer 104 with respect to a row 204 in the rows 204-214. Responsive to detecting the input with respect to the row 204, for example, the client monitoring application 234 can be configured to cause a log entry pane 228 to be displayed in the monitoring application GUI 200. The log entry pane 228 includes modification information 236, wherein the modification information 236 comprises additional details of a modification that occurred with respect to an EHR server computing device (or a feature hosted thereon) that is represented by values in the row 204. For example, the modification information 236 can include hardware specifications or changes to processors, hard drives, etc. of the EHR server computing device. Additionally, the modification information 236 can include software specifications of the EHR server computing device (operating system details, EHR versions, etc.).

Additionally, the client monitoring application 234 is configured to receive sorting input or filtering input from the EHR support engineer 104, wherein the sorting input causes the log entries table 202 to sort the rows 204-214 based upon values in a column, and wherein the filtering input causes values to be removed from the log entries table 202. For example, the sorting input can be a cursor tap on a header of the column 218. Responsive to the receiving the sorting input, the client monitoring application 234 can sort the rows 204-214 such that the rows 204-214 are sorted based upon the values in the column 218 (e.g., earliest date to latest date). It is to be understood that the sorting input can be cursor taps on the exemplary columns, wherein the client monitoring application 234 can sort the rows based upon values in an exemplary column (in the exemplary columns). In another exemplary embodiment, when the client monitoring application 234 detects input on a row or column, the client monitoring application 234 can transmit an indication that a row or column has been selected to the monitoring application 120 executing on the EHR monitoring server device 102, and the monitoring application 120 can perform the requested sorting and/or filtering. Responsive to sorting and/or filtering the data, the monitoring application 120 can transmit the sorted and/or filtered data to the support engineer computing device 103, whereupon the client monitoring application 234 causes the sorted and/or filtered data to be presented on the display 122 (in the monitoring application GUI 200).

Figure 3:
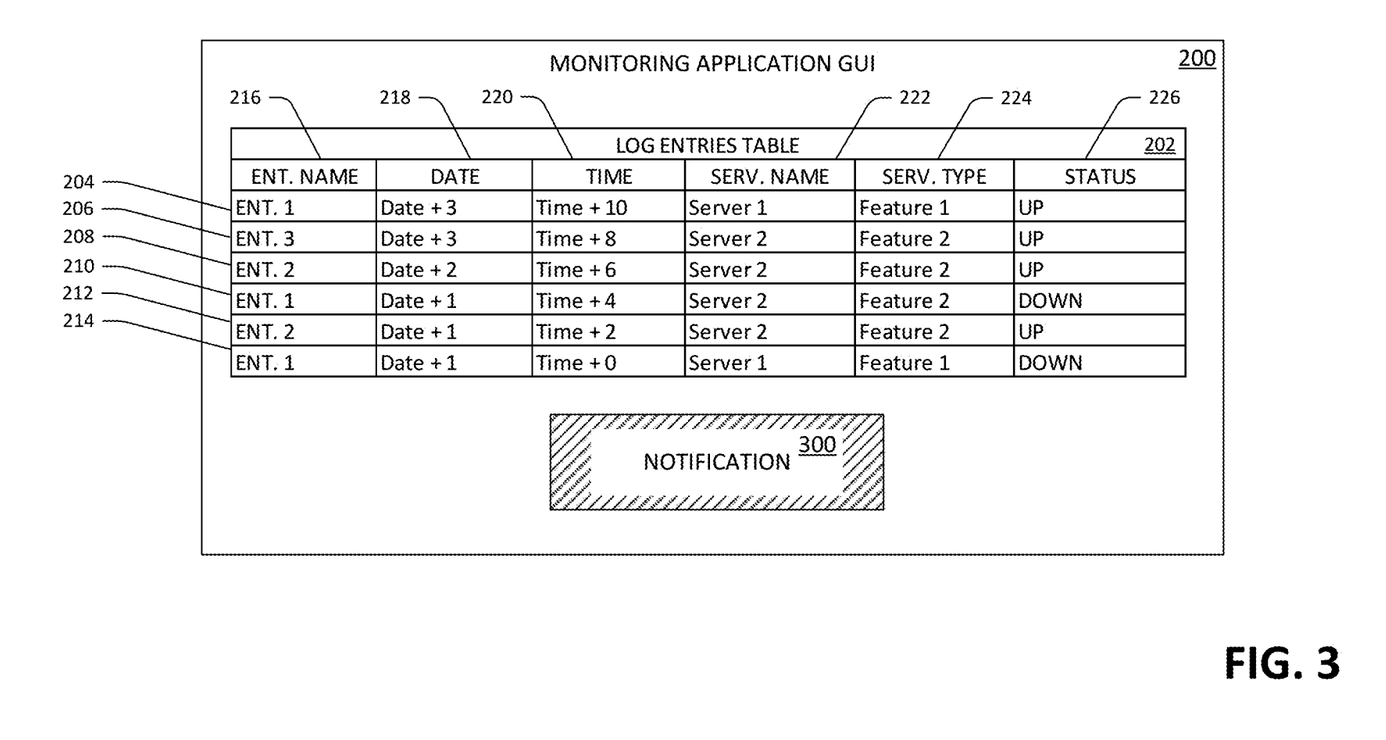
FIG. 3 is an exemplary graphical user interface (GUI) of monitoring application.

The notification component 130, as previously mentioned, is configured to transmit notifications to the support engineer computing device 103 (and thus the support engineer 104) based upon a log entry satisfying a subscription of the EHR support engineer 104. For example, the EHR support engineer 104 can subscribe to log entries that comprise information regarding a particular EHR server computing device, information regarding a particularly feature of an EHR, etc. Turning now to FIG. 3, responsive to detecting that a log entry satisfies the subscription, the notification component 130 is configured to cause a notification 300 to be displayed in the monitoring application GUI 200. The notification 300 can comprise information that is similar to, as described previously, the modification information 236.

Figure 4:
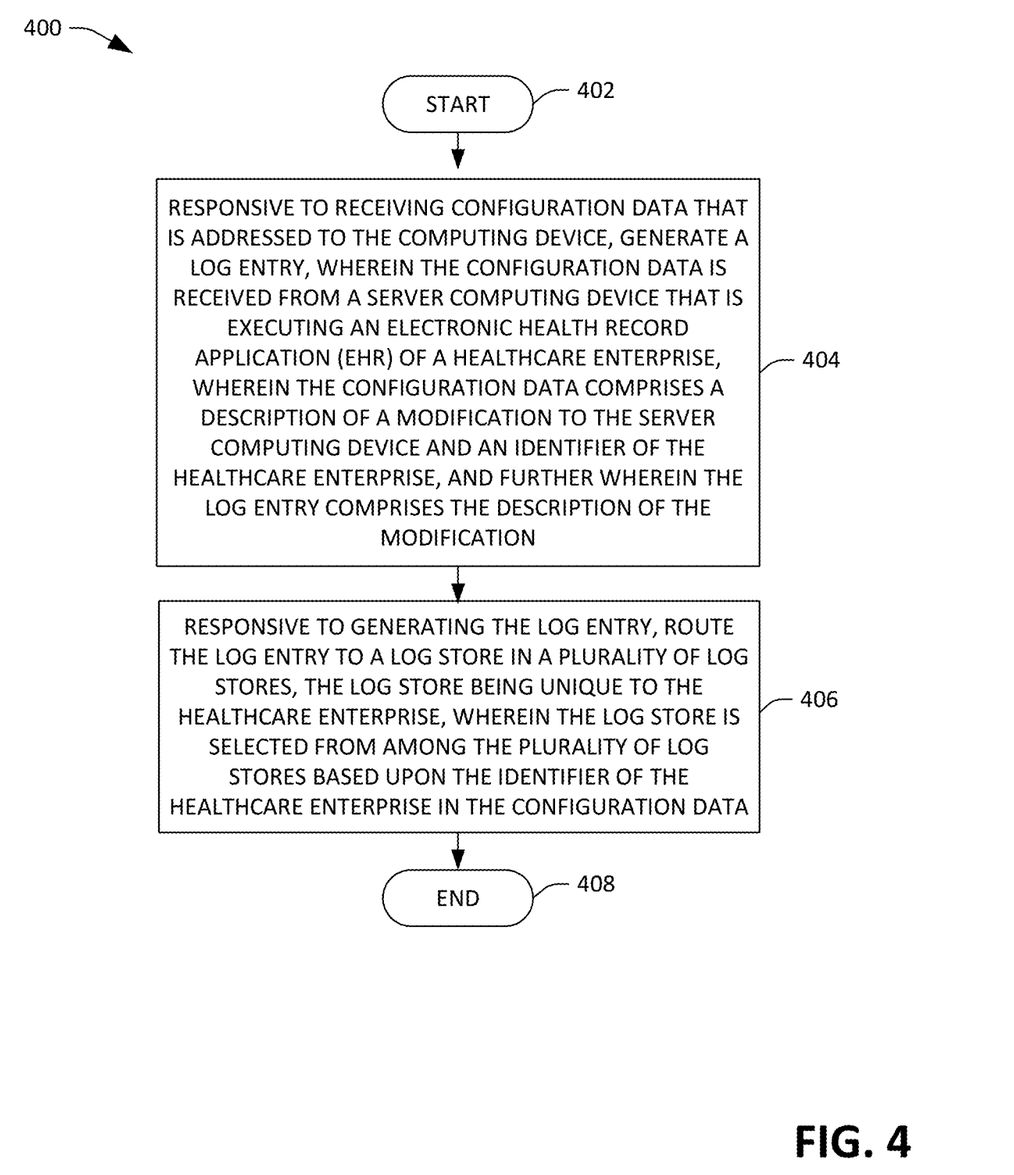
FIG. 4 is a flow diagram illustrating an exemplary methodology for generating and storing a log entry based upon configuration data received from a monitoring service, wherein the configuration data includes an indication of a modification to a server computing device.

FIG. 4 depicts an exemplary methodology pertaining to generating and storing a log entry based upon configuration data received from a monitoring service, wherein the configuration data includes an indication of a modification to a server computing device. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodology can be stored in a computer-readable medium, displayed on a display device, and/or the like.

The methodology 400 is performed at an EHR monitoring server device that executes a monitoring application. The methodology 400 starts at 402, and at 404, responsive to receiving configuration data that is addressed to the EHR monitoring server device, the monitoring application generates a log entry. The configuration data is received from a server computing device that is executing an electronic health record application (EHR) of a healthcare enterprise, where the server computing device has a monitoring service installed thereon (e.g., as part of an EHR). The configuration data comprises a description of a modification to the server computing device and/or an application installed on the server computing device, as well as an identifier of the healthcare enterprise. The log entry comprises the description of the modification.

At 406, responsive to generating the log entry, the monitoring application routes the log entry to a log store in a plurality of log stores. The log store is unique to the healthcare enterprise in that the log store comprises log entries that include the identifier of the healthcare enterprise. The log store is selected from among the plurality of log stores based upon the identifier of the healthcare enterprise in the configuration data. The monitoring application can be configured to receive additional configuration data, and generate and route additional log entries similarly as previously described. Further the monitoring application can be configured to transmit data for inclusion in a graphical user interface (GUI) on a client computing device, where the GUI comprises a visual representation of the log entry. Additionally, the monitoring application can be configured to transmit a notification of the modification to the server computing device, wherein the notification is displayed on a display and includes an indication of the modification. The methodology 400 completes at 408.

Figure 5:
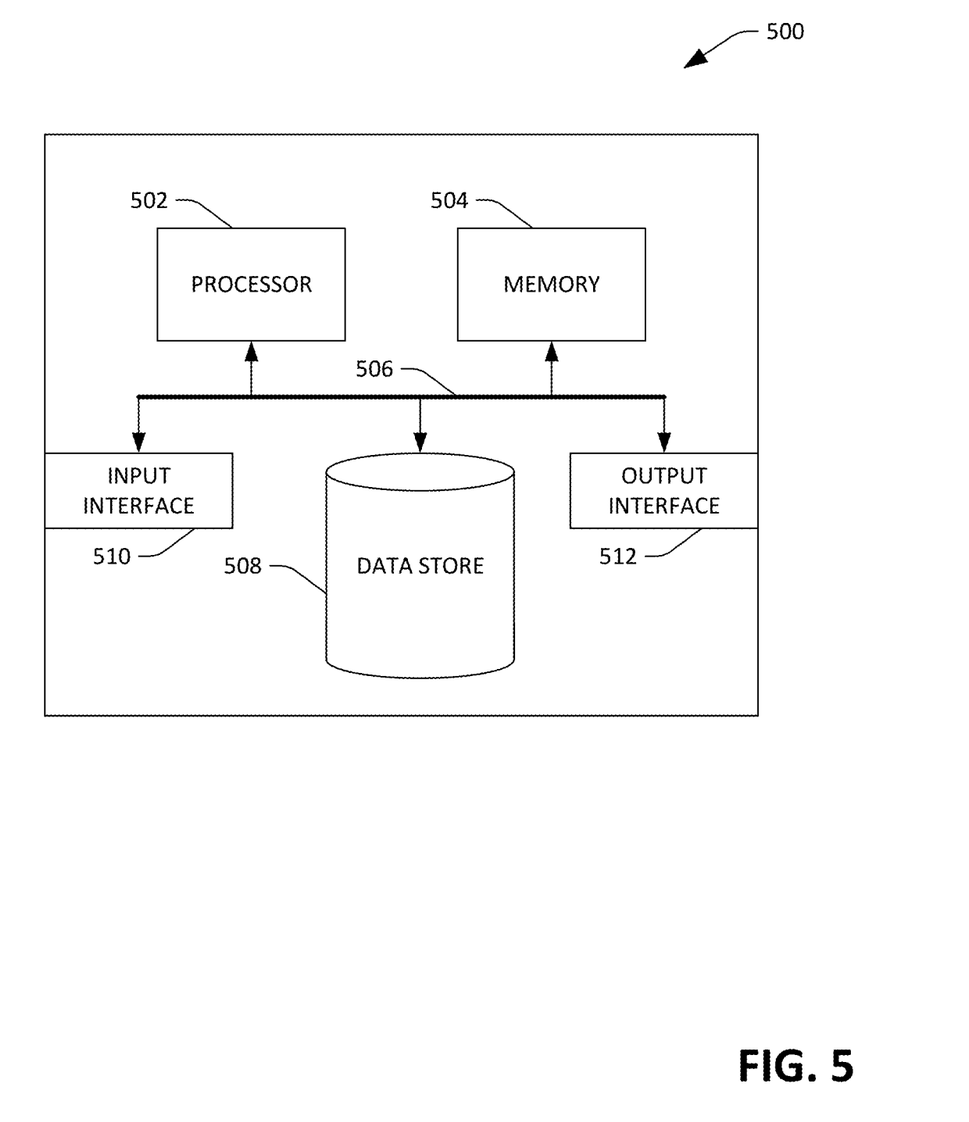
FIG. 5 is an exemplary computing device.

Referring now to FIG. 5, a high-level illustration of an exemplary computing device 500 that can be used in accordance with the systems and methodologies disclosed herein is illustrated. For instance, the computing device 500 may be used in a system that facilitates generating and presenting a log entry based upon configuration data received from a monitoring service executing at a server computing device that executes an EHR. The computing device 500 includes at least one processor 502 that executes instructions that are stored in a memory 504. The instructions may be, for instance, instructions for implementing functionality described as being carried out by one or more components discussed above or instructions for implementing one or more of the methods described above. The processor 502 may access the memory 504 by way of a system bus 506. In addition to storing executable instructions, the memory 504 can include a log entry, a log store, etc.

The computing device 500 additionally includes a data store 508 that is accessible by the processor 502 by way of the system bus 506. The data store 508 may include executable instructions, databases, etc. The computing device 500 also includes an input interface 510 that allows external devices to communicate with the computing device 500. For instance, the input interface 510 may be used to receive instructions from an external computer device, from a user, etc. The computing device 500 also includes an output interface 512 that interfaces the computing device 500 with one or more external devices. For example, the computing device 500 may display text, GUIs, etc. by way of the output interface 512.

It is contemplated that the external devices that communicate with the computing device 500 via the input interface 510 and the output interface 512 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 500 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 500 may be a distributed system. Thus, for instance, several devices may be in communication by way of a network connection and may collectively perform tasks described as being performed by the computing device 500.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A computing device that is configured to cause an electronic health record application (EHR) installed on a server computing device to be updated, the computing device comprising:
   at least one processor;
   memory that stores instructions that, when executed by the at least one processor, cause the at least one processor to perform acts comprising:
      receiving, from the server computing device, configuration data, wherein the configuration data is addressed to the computing device, and further wherein the configuration data comprises an identifier for a healthcare enterprise that is using the EHR, the configuration data includes a description of a hardware configuration of the server computing device and an identity of a version of the EHR;
      responsive to receiving the configuration data, generating a log entry in a database for the configuration data, the log entry comprises the description of the hardware configuration and the version of the EHR;
      responsive to generating the log entry, routing the log entry to a log store in a plurality of log stores, the log store being unique to the healthcare enterprise, wherein the log store is selected from among the plurality of log stores based upon the identifier of the healthcare enterprise in the configuration data;
      transmitting a notification to a client computing device based upon the log entry, the notification indicating that at least one of hardware of the server computing device or the EHR installed on the server computing device is to be updated;
      receiving, from the server computing device, second configuration data, wherein the second configuration data is addressed to the computing device, and further wherein the second configuration data comprises the identifier for the healthcare enterprise that is using the EHR, the second configuration data includes a second description of the hardware configuration of the server computing device, wherein the second description of the hardware configuration is different from the description of the hardware configuration in the configuration data;

responsive to receiving the second configuration data, generating a second log entry in the database for the second configuration data, the second log entry comprises the second description of the hardware configuration; and responsive to generating the second log entry, routing the second log entry to the log store, wherein the second log entry represents an up to date hardware configuration of the server computing device.

2. The computing device of claim 1, wherein the server computing device is executing a feature of the EHR, wherein the feature comprises at least one of:
an EHR web server;
an EHR database;
an EHR messaging application; or
an EHR interface.

3. The computing device of claim 1, the acts further comprising:
identifying that the EHR executing on the server computing device is to be updated based upon the log entry; and
transmitting a command to the server computing device that causes the EHR to be updated on the server computing device.

4. The computing device of claim 1, the acts further comprising:
transmitting the log entry for display on a client computing device, wherein the log entry is presented in a graphical user interface (GUI).

5. The computing device of claim 1, the notification is that the hardware of the server computing device is to be updated.

6. The computing device of claim 1, the notification is that the EHR installed on the server computing device is to be updated.

7. A method executed on a computing device, the method being for causing an electronic health record application (EHR) installed on a server computing device to be updated, the method comprising:
receiving, from the server computing device, configuration data, wherein the configuration data is addressed to the computing device, and further wherein the configuration data comprises an identifier for a healthcare enterprise that is using the EHR, the configuration data includes a description of a hardware configuration of the server computing device and an identity of a version of the EHR;
responsive to receiving the configuration data, generating a log entry in a database for the configuration data, the log entry comprises the description of the hardware configuration and the version of the EHR;
responsive to generating the log entry, routing the log entry to a log store in a plurality of log stores, the log store being unique to the healthcare enterprise, wherein the log store is selected from among the plurality of log stores based upon the identifier of the healthcare enterprise in the configuration data;
transmitting a notification to a client computing device based upon the log entry, the notification indicating that at least one of hardware of the server computing device or the EHR installed on the server computing device is to be updated;

receiving, from the server computing device, second configuration data, wherein the second configuration data is addressed to the computing device, and further wherein the second configuration data comprises the identifier for the healthcare enterprise that is using the EHR, the second configuration data includes a second description of the hardware configuration of the server computing device, wherein the second description of the hardware configuration is different from the description of the hardware configuration in the configuration data;

responsive to receiving the second configuration data, generating a second log entry in the database for the second configuration data, the second log entry comprises the second description of the hardware configuration; and responsive to generating the second log entry, routing the second log entry to the log store, wherein the second log entry represents an up to date hardware configuration of the server computing device.

8. The method of claim 7, wherein the server computing device is executing a feature of the EHR, wherein the feature comprises at least one of:
an EHR web server;
an EHR database;
an EHR messaging application; or
an EHR interface.

9. The method of claim 7, further comprising:
identifying that the EHR executing on the server computing device is to be updated based upon the log entry; and
transmitting a command to the server computing device that causes the EHR to be updated on the server computing device.

10. The method of claim 7, further comprising:
transmitting the log entry for display on a client computing device, wherein the log entry is presented in a graphical user interface (GUI).

11. The method of claim 7, the notification is that the hardware of the server computing device is to be updated.

12. The method of claim 7, the notification is that the EHR installed on the server computing device is to be updated.

13. A computer-readable storage medium of a computing device, the computer-readable storage medium comprising instructions that, when executed by a processor, cause the processor to perform a method for causing an electronic health record application (EHR) installed on a server computing device to be updated, the method comprising:
receiving, from the server computing device, configuration data, wherein the configuration data is addressed to the computing device, and further wherein the configuration data comprises an identifier for a healthcare enterprise that is using the EHR, the configuration data includes a description of a hardware configuration of the server computing device and an identity of a version of the EHR;
responsive to receiving the configuration data, generating a log entry in a database for the configuration data, the log entry comprises the description of the hardware configuration and the version of the EHR;
responsive to generating the log entry, routing the log entry to a log store in a plurality of log stores, the log store being unique to the healthcare enterprise, wherein the log store is selected from among the plurality of log stores based upon the identifier of the healthcare enterprise in the configuration data;

transmitting a notification to a client computing device based upon the log entry, the notification indicating that at least one of hardware of the server computing device or the EHR installed on the server computing device is to be updated;

receiving, from the server computing device, second configuration data, wherein the second configuration data is addressed to the computing device, and further wherein the second configuration data comprises the identifier for the healthcare enterprise that is using the EHR, the second configuration data includes a second description of the hardware configuration of the server computing device, wherein the second description of the hardware configuration is different from the description of the hardware configuration in the configuration data;

responsive to receiving the second configuration data, generating a second log entry in the database for the second configuration data, the second log entry comprises the second description of the hardware configuration; and responsive to generating the second log entry, routing the second log entry to the log store, wherein the second log entry represents an up to date hardware configuration of the server computing device.

14. The computer-readable storage medium of claim 13, wherein the server computing device is executing a feature of the EHR, wherein the feature comprises at least one of:
an EHR web server;
an EHR database;
an EHR messaging application; or
an EHR interface.

15. The computer-readable storage medium of claim 13, the method further comprising:
identifying that the EHR executing on the server computing device is to be updated based upon the log entry; and
transmitting a command to the server computing device that causes the EHR to be updated on the server computing device.

16. The computer-readable storage medium of claim 13, the method further comprising:
transmitting the log entry for display on a client computing device, wherein the log entry is presented in a graphical user interface (GUI).

17. The computer-readable storage medium of claim 13, the notification is that the hardware of the server computing device is to be updated.

* * * * *